(12) United States Patent
Smoliarov et al.

(10) Patent No.: US 6,802,826 B1
(45) Date of Patent: Oct. 12, 2004

(54) UNIVERSAL ANTI-INFECTIOUS PROTECTOR FOR NEEDLELESS INJECTORS

(75) Inventors: Boris V. Smoliarov, Voronezh (RU); Victor T. Rogatchev, Voronezh (RU); Victor N. Katov, Voronzeh (RU); Alan Felton, Lenexa, KS (US); Nathaniel Leon, Lutherville, MD (US)

(73) Assignee: Felton International, Inc., Lenexa, KS (US)

( * ) Notice: Subject to any disclaimer, the term of this patent is extended or adjusted under 35 U.S.C. 154(b) by 252 days.

(21) Appl. No.: 09/685,499

(22) Filed: Oct. 10, 2000

(30) Foreign Application Priority Data

Oct. 12, 1999 (RU) .............................. 99121141
Nov. 23, 1999 (RU) .............................. 99124268

(51) Int. Cl.$^7$ .............................. A61M 5/32
(52) U.S. Cl. .............................. 604/192; 604/68; 604/69; 604/70; 604/71; 604/72; 604/268
(58) Field of Search .............................. 604/192, 68, 69, 604/70, 71, 72, 198, 46, 47, 131, 218, 213, 215, 268

(56) References Cited

U.S. PATENT DOCUMENTS

| | | |
|---|---|---|
| 2,821,891 A | 2/1958 | Gorey |
| 3,057,349 A | 10/1962 | Ismach |
| 3,292,622 A | 12/1966 | Banker |
| 3,461,867 A | 8/1969 | Zimmet et al. |
| 3,515,130 A | 6/1970 | Tsujino |
| 3,518,990 A | 7/1970 | Banker |
| 3,540,444 A | 11/1970 | Moreland |
| 3,788,315 A | 1/1974 | Laurens |
| 3,853,125 A | 12/1974 | Clark et al. |
| 4,103,684 A | 8/1978 | Ismach |
| 4,124,024 A | 11/1978 | Schwebel et al. |
| 4,165,739 A | 8/1979 | Doherty et al. |
| 4,266,541 A | 5/1981 | Landau |
| 4,403,986 A | 9/1983 | Dettbarn et al. |
| 4,592,742 A | 6/1986 | Landau |
| 4,596,556 A | 6/1986 | Morrow et al. |
| 4,722,728 A | 2/1988 | Dixon |
| 4,850,967 A | 7/1989 | Cosmai |
| 4,874,367 A | 10/1989 | Edwards |

(List continued on next page.)

FOREIGN PATENT DOCUMENTS

| | | |
|---|---|---|
| EP | 0526772 | 2/1993 |
| EP | 0776224 B1 | 8/1995 |
| EP | 0888790 A1 | 7/1997 |
| EP | 0834330 | 4/1998 |
| EP | 0788386 B1 | 1/1999 |
| EP | 0888791 A1 | 1/1999 |
| EP | 0799064 | 8/1999 |

(List continued on next page.)

OTHER PUBLICATIONS

Dimache, et al., *A Clinical Epidemiological and Laboratory Study on Avoiding the Risk of Transmitting Viral Hepatitis During Vaccinations with the Dermojet Protected by an Anticontaminant Disposable Device*, Vaccine, vol. 15, No. 8, pp. 1010–1013 (1997).

Jet Gun Injection Transmission: *A Clinical Epidemiological and Laboratory Study on Avoiding the Risk of Transmitting Viral Hepatitis During Vaccinations with the Dermojet Protected by an Anticontaminant Disposable Device*, American Journal of Infection Control, vol. 26, No. 4, pp. 442–445 (Aug. 1998).

*Primary Examiner*—Teresa Walberg
*Assistant Examiner*—Fadi H. Dahbour
(74) *Attorney, Agent, or Firm*—Joseph A. Mahoney; Mayer, Brown, Rowe & Maw LLP (57) ABSTRACT

Disclosed is a medical device used to prevent the cross contamination of patients or injectors.

29 Claims, 4 Drawing Sheets

U.S. PATENT DOCUMENTS

| | | |
|---|---|---|
| 4,913,699 A | 4/1990 | Parsons |
| 5,000,737 A | 3/1991 | Free et al. |
| 5,024,656 A | 6/1991 | Gasaway et al. |
| 5,049,125 A | 9/1991 | Accaries et al. |
| 5,062,830 A | 11/1991 | Dunlap |
| 5,063,905 A | 11/1991 | Farrell |
| 5,085,647 A | 2/1992 | Henderson et al. |
| 5,152,751 A | 10/1992 | Kozlowski |
| 5,171,304 A | 12/1992 | Ris et al. |
| 5,190,523 A | 3/1993 | Lindmayer |
| 5,222,948 A | 6/1993 | Austin et al. |
| 5,256,142 A | 10/1993 | Colavecchio |
| 5,279,608 A | 1/1994 | Cherif Cheikh |
| 5,334,144 A | 8/1994 | Alchas et al. |
| 5,354,286 A | 10/1994 | Mesa et al. |
| 5,399,163 A | 3/1995 | Peterson et al. |
| 5,411,492 A | 5/1995 | Cohn et al. |
| 5,456,388 A | 10/1995 | Honstein et al. |
| 5,501,666 A | 3/1996 | Spielberg |
| 5,503,627 A | 4/1996 | McKinnon et al. |
| 5,512,043 A | 4/1996 | Verkaart |
| 5,520,639 A | 5/1996 | Peterson et al. |
| 5,536,249 A | 7/1996 | Castellano et al. |
| 5,569,189 A | 10/1996 | Parsons |
| 5,569,209 A | 10/1996 | Roitman |
| 5,573,767 A | 11/1996 | Dufour et al. |
| 5,584,182 A | 12/1996 | Althaus et al. |
| 5,593,390 A | 1/1997 | Castellano et al. |
| 5,599,302 A | 2/1997 | Lilley et al. |
| 5,618,268 A | 4/1997 | Raines et al. |
| 5,620,434 A | 4/1997 | Brony |
| 5,643,211 A | 7/1997 | Sadowski et al. |
| 5,697,917 A | 12/1997 | Sadowski et al. |
| 5,704,911 A | 1/1998 | Parsons |
| 5,713,875 A | 2/1998 | Tanner, II |
| 5,716,346 A | 2/1998 | Farris |
| 5,722,953 A | 3/1998 | Schiff et al. |
| 5,728,074 A | 3/1998 | Castellano et al. |
| 5,730,723 A | 3/1998 | Castellano et al. |
| 5,733,600 A | 3/1998 | McCabe |
| 5,746,714 A | 5/1998 | Salo et al. |
| 5,746,733 A | 5/1998 | Capaccio et al. |
| 5,769,138 A | 5/1998 | Sadowski et al. |
| 5,776,125 A | 7/1998 | Dudar et al. |
| 5,780,100 A | 7/1998 | McCabe et al. |
| 5,782,802 A | 7/1998 | Landau |
| 5,785,688 A | 7/1998 | Joshi et al. |
| 5,788,675 A | 8/1998 | Mayer |
| 5,800,388 A | 9/1998 | Schiff et al. |
| 5,803,078 A | 9/1998 | Brauner |
| 5,807,374 A | 9/1998 | Caizza et al. |
| 5,814,024 A | 9/1998 | Thomson et al. |
| 5,817,082 A | 10/1998 | Niedospial, Jr. et al. |
| 5,820,601 A | 10/1998 | Mayer |
| 5,820,621 A | 10/1998 | Yale et al. |
| 5,827,244 A | 10/1998 | Boettger |
| 5,830,193 A | 11/1998 | Higashikawa |
| 5,832,971 A | 11/1998 | Yale et al. |
| 5,833,213 A | 11/1998 | Ryan |
| 5,833,668 A | 11/1998 | Aguilar |
| 5,833,674 A | 11/1998 | Turnbull et al. |
| 5,836,911 A | 11/1998 | Marzynski et al. |
| 5,836,923 A | 11/1998 | Mayer |
| 5,839,715 A | 11/1998 | Leinsing |
| 5,840,061 A | 11/1998 | Menne et al. |
| 5,840,062 A | 11/1998 | Gumaste et al. |
| 5,846,233 A | 12/1998 | Lilley et al. |
| 5,851,198 A | 12/1998 | Castellano et al. |
| 5,858,001 A | 1/1999 | Tsals et al. |
| 5,860,957 A | 1/1999 | Jacobsen et al. |
| 5,860,961 A | 1/1999 | Gettig |
| 5,860,962 A | 1/1999 | Lewandowski et al. |
| 5,865,796 A | 2/1999 | McCabe |
| 5,899,880 A | 5/1999 | Bellhouse et al. |
| 5,922,685 A | 7/1999 | Rakhmilevich et al. |
| 5,938,637 A | 8/1999 | Austin et al. |
| 6,004,286 A | 12/1999 | Bellhouse et al. |
| 6,010,478 A | 1/2000 | Bellhouse et al. |
| 6,013,050 A | 1/2000 | Bellhouse et al. |
| D422,697 S | 4/2000 | Bellhouse et al. |
| 6,053,889 A | 4/2000 | Heinzen et al. |
| 6,056,716 A * | 5/2000 | D'Antonio et al. ............ 604/68 |
| D428,650 S | 7/2000 | Bellhouse et al. |
| 6,083,197 A | 7/2000 | Umbaugh |
| 6,102,896 A * | 8/2000 | Roser ........................ 604/218 |
| 6,224,567 B1 * | 5/2001 | Roser ........................ 604/68 |
| 6,264,629 B1 * | 7/2001 | Landau ...................... 604/68 |
| 6,270,473 B1 * | 8/2001 | Schwebel .................... 604/69 |
| 6,309,371 B1 * | 10/2001 | Deboer et al. ................ 604/68 |
| 6,383,168 B1 * | 6/2002 | Landau et al. .............. 604/268 |
| 6,406,456 B1 * | 6/2002 | Slate et al. .................. 604/68 |

FOREIGN PATENT DOCUMENTS

| | | | |
|---|---|---|---|
| EP | 0951917 A3 | 10/1999 | |
| EP | 0951917 A2 | 10/1999 | |
| FR | 2629348 | 3/1988 | |
| FR | 2641190 | 1/1989 | |
| FR | 2629348 | 10/1989 | |
| FR | 2641190 | 7/1990 | |
| RO | 0106078 | 2/1993 | |
| RO | 0108150 | 2/1994 | |
| RU | 257697 | 11/1968 | |
| RU | 373005 | 3/1971 | ............ A61M/5/30 |
| RU | 476876 | 10/1977 | |
| RU | 718111 | 2/1980 | |
| RU | 1279636 | 12/1986 | |
| RU | 2008932 C1 | 1/1990 | ............ A61M/5/30 |
| RU | 2108117 | 1/1991 | ............ A61M/5/30 |
| WO | 9734652 A1 | 9/1997 | |
| WO | 9748485 A1 | 12/1997 | |
| WO | 9810750 | 3/1998 | |
| WO | 9813087 | 4/1998 | |
| WO | 9813470 A1 | 4/1998 | |
| WO | 9821364 | 4/1998 | |
| WO | 9901168 A1 | 1/1999 | |
| WO | 9901169 A1 | 1/1999 | |
| WO | 9908689 A1 | 2/1999 | |
| WO | 9927961 A1 | 6/1999 | |
| WO | 0013573 A1 | 3/2000 | |
| WO | 0014547 A1 | 3/2000 | |
| WO | 0019982 A1 | 4/2000 | |
| WO | 0023592 A3 | 4/2000 | |
| WO | 0023592 A2 | 4/2000 | |
| WO | 0026385 A1 | 5/2000 | |

* cited by examiner

FIG.7D

UNIVERSAL ANTI-INFECTIOUS PROTECTOR FOR NEEDLELESS INJECTORS

RELATED APPLICATIONS

This application claims priority from and a benefit to, Russian Patent Application Serial No. 99121141 filed Oct. 12, 1999, now Russian Patent No. 2152227; and Russian Patent Application Serial No. 99124268, filed Nov. 23, 1999, now Russian Patent No. 2152228, in the Federal Institute of Industrial Property of the Russian Federation, the disclosure of which is incorporated by reference herein.

TECHNICAL FIELD OF THE INVENTION

This invention relates to injection devices including, injection devices for intradermal, subcutaneous and intramuscular injections.

BACKGROUND

The most effective measure to prevent many diseases is the mass immunization with vaccines. Since medical science has come to understand the principles of viral theory and its importance to the transmission of diseases, the need to break the viral or bacterial transmission chain from host to host has become well-established. There are wide varieties of methodologies accepted by medical science to break the chain depending on the requirements of the situation. The most stringent protocols include: sterilization, disinfection, and sanitation utilizing heat chemicals and/or ionizing radiation.

Barriers are another common protocol and can be as simple as establishing an imaginary boundary where one side of the boundary is kept clean and the other is defined as contaminated. Any object being transferred from the clean to the contaminated side of the boundary is not returned to the clean side without being disinfected, sanitized, or sterilized. A typical example of this type of protocol is within the medical surgical fields. The surface of the operating table is defined as the boundary. Any item that is dropped below the surface of the operating table is immediately defined as contaminated. This includes surgical implements or the surgeon's hands.

With needle injection devices there are two common protocols both of which start from the premise that a used syringe is, by definition, contaminated. The first, which is commonly used in dentistry, uses syringes and sometimes needles that are sterilized after each use. The second is more commonly used in general medicine in the U.S. and other developed countries. This is the disposable syringe and needle assembly. Because of the low cost of production typically—less than $0.10 per syringe assembly—this protocol is well-accepted.

Jet injector systems on the other hand continue to be characterized by relatively high cost per injection ($1.00 or more) when the syringe portion of the injector is discarded with each use. Additionally, there is the challenge in developing countries where lack of understanding of viral theory and/or a general hoarding mentality discourages following generally accepted protocols within all aspects of health and hygiene. With the identification of blood-borne pathogens like HIV, Hepatitis B, Hepatitis C and others, the need to follow proper protocols becomes more critical.

In the past, jet injectors such as Ped-O-Jet®, Ammo-Jet®, and similar mass campaign jet injectors were brought to health care systems. Such injectors had no provision for preventing the transfer of blood-borne pathogens except through the complicated disassembly and disinfecting process. In mass immunization campaigns these types of injector systems fell out of favor starting in the mid and late 1980's when it was determined that bodily fluids are easily transmitted from one patient to another.

To eliminate the possible transmission of blood-borne pathogens between individuals, disposable or partially disposable jet injector systems were developed. Bio-Jet®, J-Tip®, and others characterize this type of jet injector. General acceptance of these units is limited by relatively high direct costs, even in developed countries like the United States. The standard paradigm of breaking the contamination transmission chain has been addressed by either syringe disposal or designing the syringe so it can easily be decontaminated. Currently, there exists a steadily growing danger of the epidemic diseases (AIDS, hepatitis, tuberculosis and other viral diseases transferred through blood) being transmitted between individuals through the use of needleless injectors.

The traditional needleless injectors comprise the basic design, a housing with an inner power unit, a medication unit, and a nozzle. The function of the power unit pumps the medication into an under-plunger cavity of the medication unit chamber and to expel the medication through the nozzle.

At the initial stage of needleless injector development, when no check valves were used as a control for the functioning of the medication chamber, a method to prevent foreign particles from entering the injector nozzle was to use a sealed nozzle cap. Such cap was limited by the filling of the medication chamber with medication and could not guarantee contamination prevention.

Another approach to the contamination prevention problem has been the use of a disposable, low cost, one-shot nozzle assembly for jet injectors. The nozzle assembly comprises a two-piece molded device incorporating a generally cylindrical nozzle body having a central longitudinal bore of a predefined diameter, extending from a proximal end of the nozzle towards its distal end, terminating in a conical portion of the nozzle. A very small diameter jet-forming bore is formed at the apex of the conical portion of the bore in general. The disadvantage of this device is its lower efficiency (i.e., low vaccination rate) because of poor flow due to the conical design. Moreover, a plastic nozzle element also increases the vaccination cost.

A typical jet injector design has additional drawbacks. Even in the practice of using a protective cap, there is a possibility of infection transfer from one person to another by means of fluids (blood, lymph, medication) reflected from the skin surface during injection ("back splash") that may get on the nozzle and be transferred from one patient to the next. The protective cap can be a one-shot cap, including the injection nozzle. A purpose of this device is to prevent the multiple use of a cap with a nozzle. This is achieved through the removal, replacement, and/or destruction of the cap at the later stage of the injection. However, cross-contamination continues to be problematic because in the injection stage, the contaminated matter can be transferred through the nozzle to inside the injector such as, for example, into the cavity and be transmitted to a new patient through a new cap and nozzle.

With all the known devices, there is no guarantee that the minimum safety requirements for cross-contamination prevention, as recently introduced (Glenn Austin et al., *Gross Contamination Testing of Vaccine Jet Injectors, A*

*Preliminary Report*, PATH, Seattle, Wash., 98109), will be achieved. Other studies indicate a very dangerous situation. For example, Russian and Brazilian studies have shown unfavorable data in up to 1.0% of the subjects studied—a level of risk far too great to ignore.

When jet injectors were introduced in the 1940's, they were popular for needle phobic patients or small veined patients. Improvements permitted jet injectors to administer hundreds of millions of vaccinations that saved countless lives. However, when the discovery of pathogen transfer occurred, jet injectors fell out of favour to such an extent that the WHO and the U.S. Department of Defense no longer recommended jet injector.

For example, in the mid-1980's an outbreak of Hepatitis B was caused by use of one high workload injector in a weight loss clinic. See, Canter et al., An Outbreak of Hepatitis B Associated With Jet Injections In A Weight Loss Clinic, Arch. Intern. Med., 150:1923–1927 (1990).

Present parenteral injection technology has recently been deemed by the World Health Organization (WHO) to be incompatible with their requirements for the planned Global Programme of Vaccination and Immunization (GPV) initiatives. It is estimated that 6 additional parenteral vaccines will be recommended for childhood vaccination by the year 2005, requiring a total of 3.6 billion immunization injections per year. The total number of parenteral injections, including injected drugs as well as vaccines, will be roughly ten times this number. This is in addition to the hundreds of millions needed in military induction centers, epidemic situations, worldwide immunizations, and veterinary uses. Major health care providers such as UNICEF, the WHO and CDC have recently confirmed that a radical new technology is required that can be used by personnel with minimal training and that is safer, more convenient, and more comfortable than the syringe and needle. (Jodar L., Aguado T., Lloyd J. and Lambert P-H,(1998) Revolutionizing Immunizations Gen. Eng. News 18, p. 6.)

In other words, what used to be a continent wide life saver, became an undesirable product. The present invention solves problems associated with pathogen transfer and solves many problems associated with the high costs of disposable units.

Accordingly, there is a need in the art of needleless injection devices to solve the problem of cross-contamination during mass vaccinations. More particularly, there is a need for a protector designed for the nozzle head of needleless injectors, which halts "back splash" contamination, and which is low enough in cost to ensure its practical application as a disposable unit even for mass vaccinations.

SUMMARY OF THE INVENTION

The preceding problems are solved and a technical advance is achieved by the present invention. Disclosed is an injector device in which a protective layer in conjunction with other components is used to minimize or eliminate back splash contamination.

DETAILED DESCRIPTION

Figure 1A:
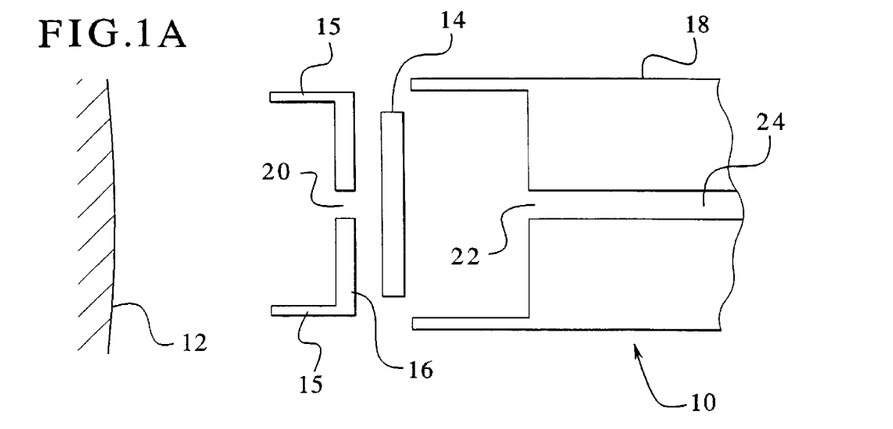
FIG. 1A demonstrates an exploded view of a simple embodiment of the present invention.

FIG. 1A demonstrates an exploded view of the present invention. An injector assembly 10 is shown. One purpose of the injector assembly 10 is to provide needless injection of medicaments into the skin 12. As described herein, the injector assembly 10 is provided with a layer, such as protective layer 14. The protective layer 14 generally comprises a material that is adapted to permit the injection of medicaments in one direction, yet minimize or retard the reverse flow. In this regard, the protective layer 14 can serve as a back splash guard. In this particular, exemplary, and non-limiting embodiment, an optional baffle 16 is provided to facilitate the diminution of back splash. The source of the medicament jet stream is from the injector 18. Common injectors include Med-E-Jet®, Ped-O-Jet®, Ammo-Jet®, and the like. The baffle 16 further comprises a baffle orifice 20, which can take any desired shape or size, depending on the intended use. In this regard, the size of the baffle orifice 20 will influence how much back splash hits the protective layer 14. It is contemplated in all embodiments that the size of the baffle orifice 20 can be sized to minimize disruption of the medicament jet stream yet maximize the protection afforded by the protective layer 14. If the baffle orifice 20 is too small, the baffle 16 may disrupt the jet stream and thereby reduce the energy of the stream. If too much diminution of the stream energy occurs, then the jet stream will not penetrate the skin 12 in the desired fashion to the desired depth.

Baffle 16 can be sized to accommodate the needed configuration, and may 10 optionally include baffle wings 15. Of course the length and diameters may vary significantly, but in one example, baffle 16 can be approximately greater than 11 mm in diameter and 5 mm tall. Generally, the diameter of the baffle orifice 20 should be slightly larger than the diameter of the jet stream. Therefore, it does not really matter how large the baffle orifice is so long as it is slightly larger than the jet stream diameter, irrespective of the diameter of the injector orifice 22.

Injector 18 has an injector orifice 22 at the distal end of the injector canal 24. The medication sought to be injected travels through the injector canal 24, exits through the injector orifice 22 and punctures the protective layer 14. The medication jet stream then enters the baffle orifice 20 and impacts the skin 12. The energy of the jet stream is chosen to provide the desired injection, depth, and location. For example, for a deeper injection, a higher energy will be necessary. The medicament jet stream then enters the skin 12 and travels to the desired situs. However, the impact on skin 12 is not without some attendant consequences. One consequence is that surface tissue, fluids, cells, and cellular contents are removed or ablated from the surface of skin 12 and fly about. This back splash of debris can travel back along the jet stream and impact the baffle 16 and protective layer 14. The debris, though, is generally not traveling fast enough to re-puncture the protective layer 14. In this regard, the protective layer 14 retards or minimizes the debris back splash into the injector orifice 22 and the injector 18. One function of the layer 14 is to prevent the contamination of the injector. In this regard, the simple concept of the invention is to protect the injector orifice 22 from contamination. Thus, in the event no baffle 16 is used, the injector itself may bear the protective layer 14. Thus, a first component can comprise at least the injector, the baffle, or the insert.

The material chosen for the layer 14 may comprise any material that facilitates a fluid stream puncture in one direction, yet retard the fluid stream puncture in the opposite direction. For example, the layer 14 can comprise a biochemically inert material that is approved for contact with pharmaceuticals, such as but not limited to, at least one of a plastic, rubber, polymer, polyethylene, polytetrafloroethylene, polyurethane, polypropylene, polyolefin, and polysulfone material. In this regard, a material that permits the perforation by the jet stream in one direction but then seals upon itself after the jet stream stops is more desirable. The protective layer or layers are desirably thin, for example greater than 0.001 mm. Preferably and non-exclusively, the thickness can range in the about 0.004 to 0.08 mm range with a further thickness of about 0.2 to 0.5 mm. It should be noted that the thickness chosen is variable. Protective layer 14 may also be textured, woven, braided, or so configured to provide a better adhesion, if necessary, or to provide better attachment, or to prevent or minimize movement. For example, the layer may have grooves of various types. As mentioned, the diameter of the protective layer (if a disc, or the width if a strip) should be slightly larger than the diameter of the jet stream.

As shown in FIG. 1A, the components are in exploded view. In assembly, the baffle 16 can be designed to fit within the injector 18 and sandwich the layer 14 generally between the baffle 16 and injector 18. Desirably, the injector orifice 22 and baffle orifice 16 should line up to minimize any diminution of the stream energy. As with any connection and assembly herein, the baffle 16 can be adapted to provide a friction fit, snap fit, screw fit, or bayonet fit. Any component herein can also be heatsealed to fit. Protective layer 14 can be also adhered, bonded, or otherwise attached to the injector 18, baffle 16 or to any part as desired.

Figure 1B:
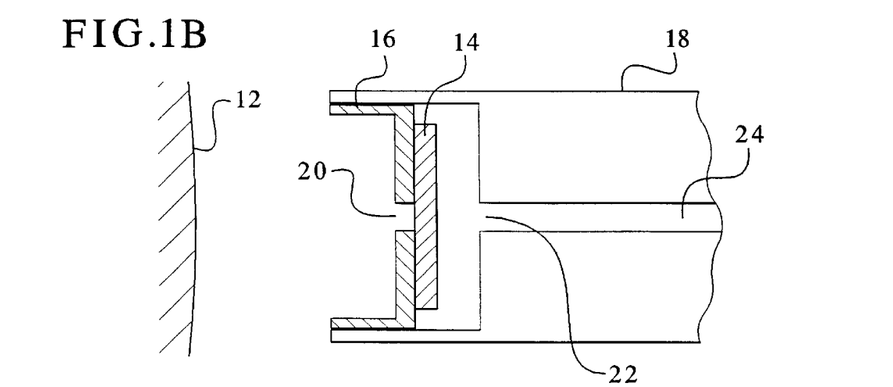
FIG. 1B demonstrates the simple embodiment in assembled form.

FIG. 1B demonstrates a simple embodiment of the present invention. As one can see, the protective layer 14 can be generally sandwiched between baffle 16 and the injector 18. The protective layer 14 can be totally sandwiched or partially sandwiched between the components described herein. As the medication is injected out through injector canal 24 and injector orifice 22, it will penetrate through the layer 14 and through the baffle orifice 20.

It should be noted that in any embodiment of the present invention, the medication need not be liquid. In addition to aqueous solutions, the present invention may employ suspensions, aqueous gels, emulsions, or controlled release injectable medications. One other dosage form includes powder. For example, Powderject Pharmaceuticals, of Oxford, United Kingdom, and/or Powderject Vaccines (Madison, Wis.) have developed an injector that propels medicine in powder form in the same manner as traditional needleless injectors. For example, see, U.S. Pat. Nos. 5,733,600; 6,053,889; and 5,899,880; the disclosures of which are expressly and entirely incorporated herein. Since the powder form of drugs take up less than 1% of the volume of drugs in liquid form, adapting the powder injectors to be used in accordance with the present invention is also contemplated. Generally, but not exclusively, the powder particles of one dose can range in size but are generally 50 microns wide, as compared to a 500 micron wide syringe needle. In other words, powder form vaccines, such as recombinant DNA based vaccines, including Hepatitis B and HIV vaccines, and other medications for treating influenza, tetanus, erectile dysfunction, allergies, pain, cancer, etc., are contemplated. Such powder forms may be admixed with small amounts of sterile water or other physiologically acceptable diluents (e.g., about 1–10%) to form pastes or suspensions. Therefore, adapting the powder injectors to have a protective cap and/or film consistent with the present invention is within the ordinary skill in the art.

Figure 2:
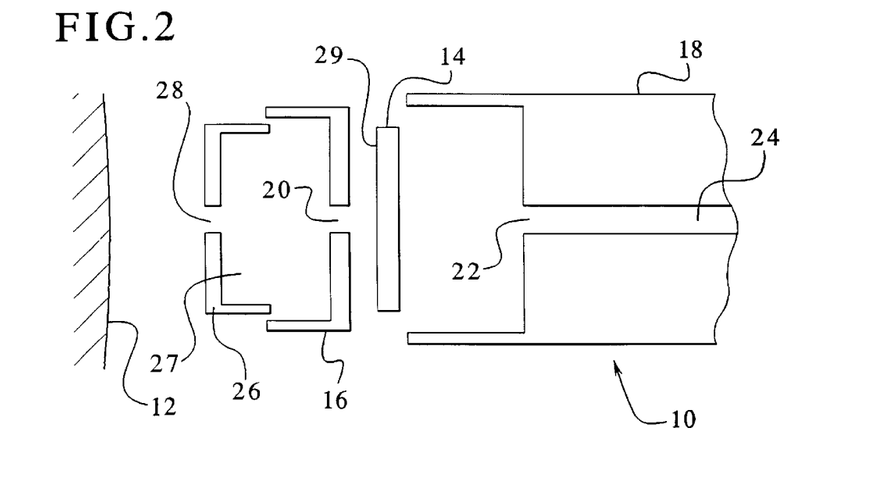
FIG. 2 shows an exploded view of another embodiment of the present invention in which another component is introduced.

FIG. 2 demonstrates another embodiment of the present invention. The injector assembly 10 is shown having a baffle 16 and an insert 26. The insert 26 can be adapted to form an insert reservoir 27. Insert 26 also has an insert distal orifice 28. Insert 26 can be adapted to fit with baffle 16 such that the insert 26 provides an additional benefit of back splash protection, during or after the injection is completed. Insert 26 can be adapted to fit with baffle 16 such that insert 26 helps to properly tension the skin for the injection type (intramuscular, subcutaneous, or intradermal). As shown in this particular, exemplary, and non-limiting embodiment, the protective layer 14 is generally located between, either partially or completely, the baffle 16 and the injector orifice 22. In this configuration, the jet stream will exit the injector orifice 22, penetrate through the layer 14, and exit through the baffle orifice 20 and insert distal orifice 28 to impact the skin 12. The skin debris will back splash against the insert 26 and any debris that flies into the insert distal orifice 28 will likely be stopped by the baffle 16. In the event that debris trajectory permits debris to travel through the baffle orifice 20, the debris will impact the distal surface 29 of layer 14.

In this regard, the injector orifice 22 is protected against contamination. The debris that hits the protective layer distal surface 29 will likely fall into the insert reservoir 27 and collect there. Insert 26 can be adapted to fit into the baffle 16 as needed. One benefit of the insert configuration is the disposability of the unit. As for configuration, the injector orifice 22 can be some distance away from the skin 12. For example, it can be adjacent the skin 12 (where a baffle or insert is not used and the layer 14 is attached directly to the injector 18), or millimeters away, such as 2–15 mm away. Naturally the distance chosen will reflect on the stream energy. Desirably, the injector orifice 22 distance from the skin 12 is chosen with this in mind. In some configurations, the proximal face of the baffle could be millimeters away from the skin, such as 2–15 mm and desirably 2–7 mm. Insert orifice 28 diameter is also sized accordingly, such as 0.001 mm or greater. In one commercial embodiment, however, the insert 26, baffle 16, and protective layer 14 can be discarded as a unit upon contamination.

Figure 3:
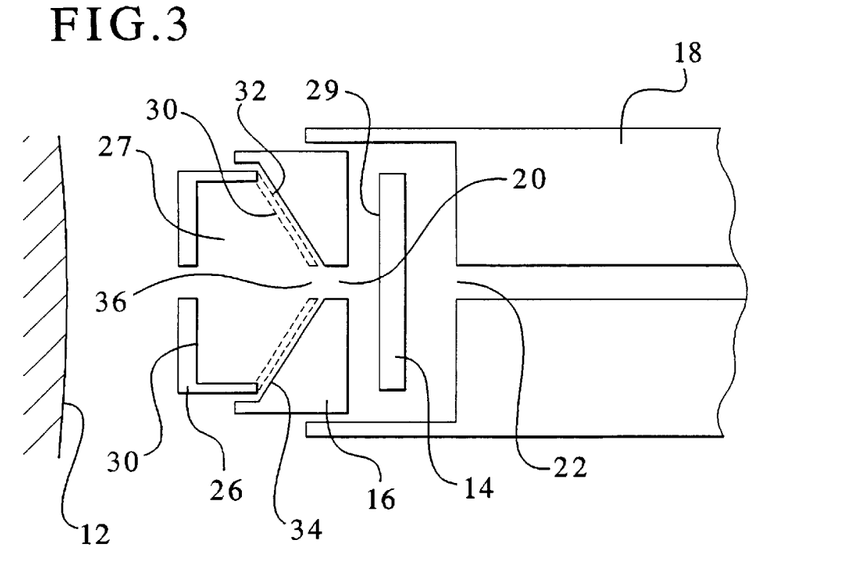
FIG. 3 shows an exploded view of another embodiment of the present invention in which some components are modified.

FIG. 3 represents another embodiment of the present invention. Shown are the baffle 16, insert 16, protective layer 14, and injector 18. In this configuration the baffle 16 is adapted to provide a greater surface area exposed to potential back splash. The insert 26 is also adapted to minimize back splash contamination. For example, insert 26 has an insert inner surface 30 and an insert outer surface 32. As shown in dotted lines, the insert 26 can be configured to form "wings" in which the insert 26 will cooperate with the baffle 16. Baffle 16 has a baffle inner surface 34 that cooperates with the insert 26. As shown in this embodiment, the insert outer surface 32 is in cooperation with the baffle inner surface 34. The wings of the insert 26 come into proximity of each other to form an insert proximal orifice 36. In this embodiment, any back splash of skin debris entering the insert distal orifice 28 will likely hit the insert inner surface 30, or the baffle inner surface 34, or the distal surface 29 of protective layer 14. In the event insert 26 is configured to not have wings, any debris can still hit the insert inner surface 30, the baffle inner surface 34, or the distal surface 29 of protective layer 14.

Figure 4:
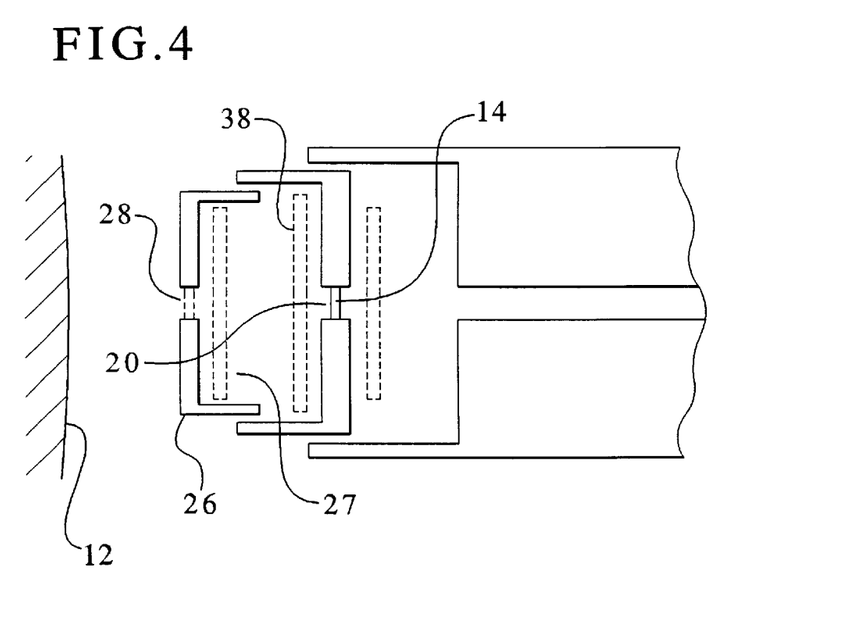
FIG. 4 shows another embodiment of the present invention in which a protective layer is shown at various positions.

FIG. 4 demonstrates yet another embodiment of the invention. Shown is a plurality of protective layers 14 shown in phantom 38. In this exemplary and non-limiting embodiment, the protective layer 14 is shown covering the baffle orifice 20. The protective layer 14 can be integrally formed with the baffle 16 or can be separately affixed to the baffle 16. In this embodiment, the removal of the baffle 16 facilitates disposability. Also shown is that multiple protective layers are present. Protective layers can be generally found proximal the skin, coincident with the insert distal orifice 28, proximal to the insert distal orifice 28, distal to the baffle 16, distal to the baffle orifice 20, coincident with the baffle orifice 20, or proximal to the baffle orifice 20. The number of protective layers can be chosen to maximize the jet stream energy for puncture purposes, but diminish back splash contamination potential. Also shown in FIG. 4 is the assembly in which the insert 26 and baffle 16 are within the injector assembly 18. Where multiple layers are used, the layers can be attached using bonding, heatsealing, or sandwiching the layers.

Figure 7A:
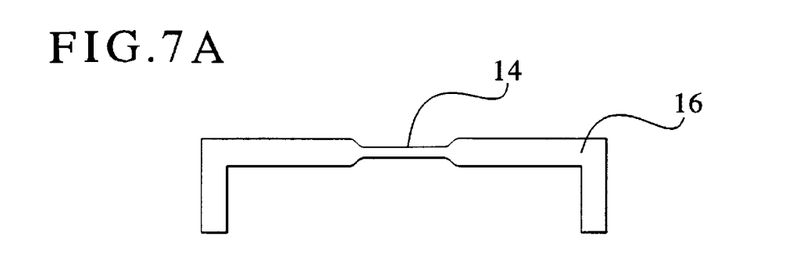
FIGS. 7A–D depict several different embodiments of the protective layer of the present invention.
Figure 7B:
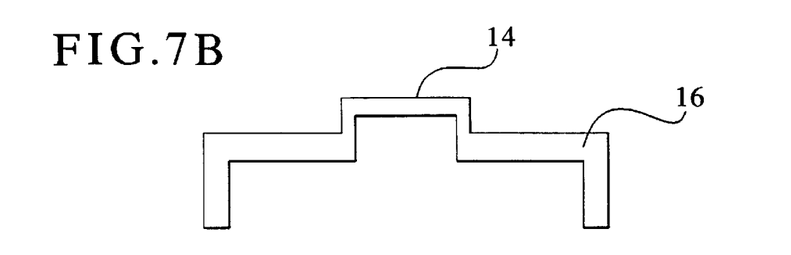
Figure 7C:
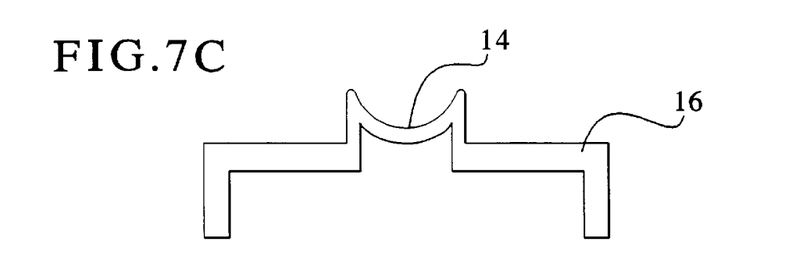
Figure 7D:
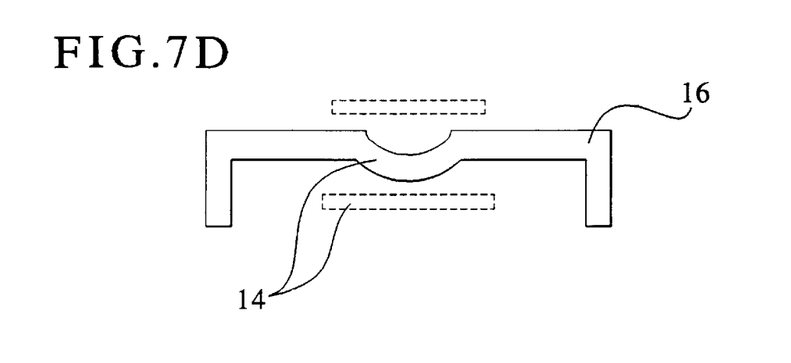

As seen in FIGS. 7A–D, it should be noted that in any embodiment herein, the protective layer 14 or film need not be a separate piece. Rather it may be integrally formed with a component, such as a septum. For example, the protective layer 14 may be part of the baffle 16 in which that area that will be punctured by the jet stream is adapted to give way during injection. For example, if the baffle 16 is made of plastic, then the area that will serve as the protective layer can be integral with the baffle 16 yet be "ground" down slightly to make it thinner or more easily adapted to perforation. In yet another embodiment, the layer 14 may be separately manufactured then adhered in some fashion to a component, such as the baffle 16. In yet another embodiment as shown in FIG. 7D, a plurality of films may also be used (as shown in phantom lines).

Figure 5:
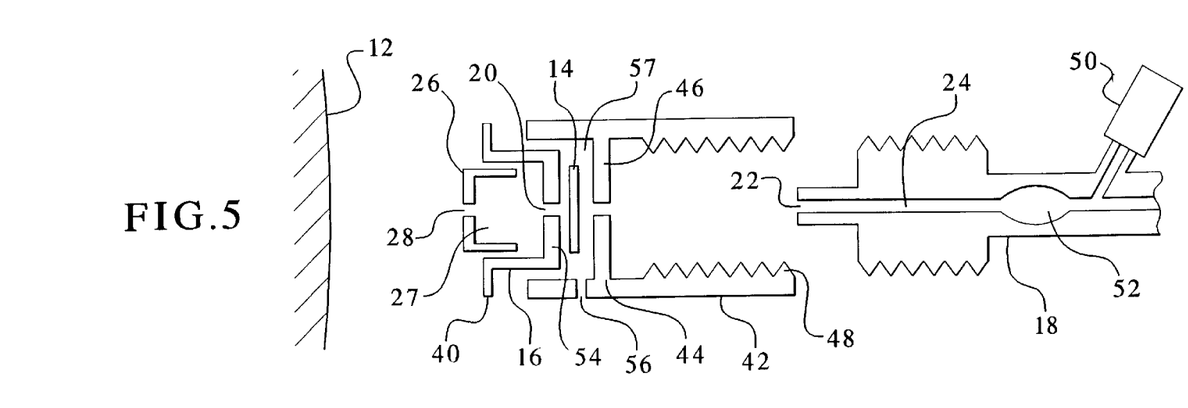
FIG. 5 shows yet another embodiment of the present invention in which an intermediate piece is shown.

FIG. 5 demonstrates yet another embodiment of the present invention. Baffle 16 is provided with a plurality of baffle legs 40. The baffle legs 40 can be adapted to cooperate with an intermediate piece 42. The intermediate piece 42 has a proximal and distal end such that various components can be attached to either or both ends. In this particular, exemplary, and non-limiting embodiment, intermediate piece 42 has an intermediate piece orifice 44 therethrough. This intermediate piece orifice 44 can be formed by one or more intermediate piece extensions 46. As with any orifice described herein, the size and shape of the orifice may determine the potential back splash contamination and the interruption of the jet stream energy. Intermediate piece 42 can be connected to injector 18 and/or baffle 16 and/or insert 26 via an intermediate piece connector 48. The intermediate piece connector 48 can include any mechanism to attach one piece to another, and can further include a friction fit, bayonet, or screw fitting.

Therefore, as medication is extracted from the medication vial 50, it is drawn into the injector chamber 52 wherein the injection system then delivers the medication through the injector canal 24, through the injector orifice 22, into the intermediate piece 42, through the intermediate piece orifice 44, and then through the various distal components. As shown in FIG. 5, upon exiting the intermediate piece orifice 44, the medication will penetrate the protective layer 14 and then enter the baffle 16 via the baffle orifice 20, then through the insert reservoir 27, through the insert distal orifice 28, to then impact the skin. Skin debris, if it has the correct trajectory, can enter the insert 26-baffle 16 component. Debris can either strike the baffle 16, such as baffle splash guards 54, or insert 26 itself, or can strike the protective layer distal surface 29. In the event that the debris has sufficient energy to re-puncture the layer 14, debris will then strike the intermediate piece 42, such as the intermediate piece extensions 46. In this manner, the only manner in which the injector tip is contaminated is if the debris enters the intermediate piece 42 at such a precise trajectory that is flies through the orifice 44 and directly hits the injector orifice 22. However, although not shown in FIG. 5, a plurality of protective layers 14 can be used at various stages along the insert 26, baffle 26, or intermediate piece 42. Intermediate piece can also include an optional intermediate piece channel 56, which fluidly communicates with the atmosphere and the intermediate piece lumen 57. This permits an equalization of pressure in the lumen 57 and also permits any debris in the lumen 57 to be evacuated. As for size, intermediate piece channel can be approximately any size but may be about 1 mm.

Therefore, the injector assembly 10 provides increased resistance to contamination using a variety of components. It is noted that in any and all embodiments described herein, no individual component is critical or necessary for accomplishing the invention. For example, the embodiment of FIG. 5 can be configured so that it does not have an insert 26, a baffle 16, a protective layer 16, or the intermediate piece 46. In FIG. 5, the addition of the insert 26 and baffle 16 provide added benefit.

Figure 6:
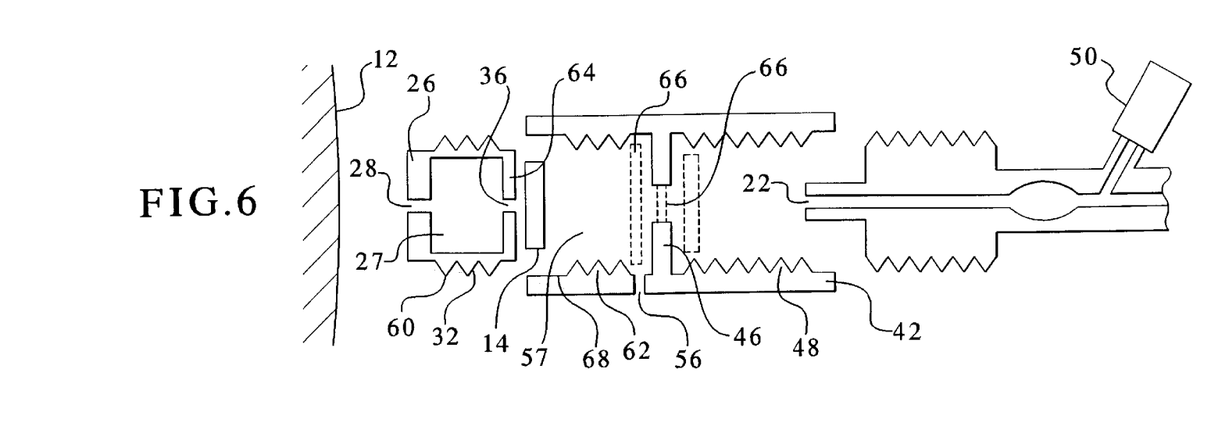
FIG. 6 shows yet another embodiment of the present invention in which a protective layer is shown at various positions.

FIG. 6 demonstrates yet another embodiment of the present invention. In this embodiment, an insert 26 plays many roles. First, the insert 26 is provided with an insert connector 60, shown here by example only, as a screw fitting. The intermediate piece 42 is provided with an intermediate piece distal connector 62, as shown by example only, as a screw fitting. Accordingly, the intermediate piece distal connector 62 cooperates with the insert connector 60 to provide a detachable attachment. The insert 26 is adapted to provide the same characteristics as the baffle 16 (not shown) in that it can be adapted to also have an insert splash guard 64. While the protective layer 14 is shown proximal to the insert 26, the intermediate piece 42 can also include an intermediate piece protective layer 66 located anywhere along the intermediate piece 42. This intermediate piece protective layer 66 is shown in phantom either distal to the intermediate piece orifice 44, coincident with the orifice 44, or proximal to the orifice 44. In this regard, the intermediate piece protective layer 66 is distal to the injector orifice 22. In operation, the debris that enters the insert 26 will likely impact the insert splash guard(s) 64, the protective layer 14, the intermediate piece extension(s) 46, or the intermediate piece protective layer 66. In this regard, the disposability of the components is enhanced in that the intermediate piece inner surface 68 remains generally clean in that most debris stays within the insert 26 or strikes the protective layers 14, 66.

It is to be understood that although the invention herein described is only illustrative. None of the embodiments shown herein are limiting. It is apparent to those skilled in the art that modifications and adaptations can be made without departing from the scope of the invention as defined by the claims appended.

What is claimed is:

1. An injector assembly, comprising:
   a) an injector having a proximal end and a distal end, the injector comprising an injector orifice at the distal end;
   b) a first component, the first component having an orifice therethrough, the first component generally located at the injector distal end;
   c) a second component, the second component having an orifice therethrough, the second component generally located at the injector distal end; and
   d) a protective layer generally located at the injector distal end covering at least one of the injector orifice, the first component orifice, or the second component orifice;
   wherein the first component, the second component, and the protective layer are configured at the distal end of the injector to block the splashback of debris from entering the injector orifice during and/or after injection.

2. The injector assembly of claim 1, wherein the first component is a baffle.

3. The injector assembly of claim 1, wherein the first component is an insert.

4. The injector assembly of claim 1, wherein the second component is a baffle.

5. The injector assembly of claim 1, wherein the second component is an insert.

6. The injector assembly of claim 1, wherein the first component is proximal to the second component.

7. The injector assembly of claim 1, wherein the protective layer is proximal to either the first component or the second component.

8. The injector assembly of claim 1, wherein the protective layer is proximal to the first and second components.

9. The injector assembly of claim 1, wherein the protective layer is proximal to the second component and distal to the first component.

10. The injector assembly of claim 1, wherein the protective layer covers at least one of the first component orifice and the second component orifice.

11. The injector assembly of claim 1, wherein the injector assembly includes a plurality of protective layers.

12. The injector assembly of claim 11, wherein at least one of the plurality of protective layers is distal to the first or second component.

13. The injector assembly of claim 1, wherein the first component is a baffle, the second component is an insert, and the protective layer is distal to the first component.

14. A medical device, comprising:
   a) a first component, the first component having an orifice therethrough;
   b) a second component, the second component having an orifice therethrough, the second component being partially distal to the first component;
   c) an intermediate piece; and
   d) a protective layer, the protective layer located generally between the intermediate piece and the second component orifice.

15. The medical device of claim 14, wherein the intermediate piece further comprises a connector component.

16. The medical device of claim 15, wherein the connector component further comprises at least one of a friction fit, bayonet, and screw type connector.

17. The medical device of claim 16, wherein the intermediate piece further comprises a connector component at each end of the intermediate piece.

18. The medical device of claim 15, wherein the intermediate piece further comprises a connector component at each end of the intermediate piece.

19. The medical device of claim 14, wherein the assembly further comprises an injector.

20. The medical device of claim 19, wherein the injector further comprises a connector component.

21. The medical device of claim 20, wherein the injector connector component is adapted to engage the intermediate piece.

22. The medical device of claim 20, wherein the protective layer is distal to the injector.

23. The medical device of claim 22, wherein the intermediate piece further comprises an orifice extending therethrough.

24. The medical device of claim 23, wherein the intermediate piece orifice is generally coincident with the first and second component orifices.

25. The medical device of claim 24, wherein the protective layer is distal to the injector and proximal to either the first or second component.

26. An injector assembly, comprising:
   a) an injector having a proximal end and a distal end, the injector comprising an injector orifice at the distal end;
   b) a first component, the first component having an orifice therethrough, the first component generally located at the injector distal end;
   c) a second component, the second component having an orifice therethrough, the second component generally located at the injector distal end; and
   d) a plurality of protective layers generally located at the injector distal end.

27. The injector assembly of claim 26, wherein at least one of the plurality of protective layers is distal to the first or second component.

28. The injector assembly of claim 26, wherein at least one of the plurality of protective layers is proximal to the first or second component.

29. The injector assembly of claim 26, wherein at least one of the plurality of protective layers is integrally formed with at least one of the first component or the second component.

* * * * *